United States Patent
Small

[11] Patent Number: 5,914,025
[45] Date of Patent: *Jun. 22, 1999

[54] ION CHROMATOGRAPHIC METHOD AND APPARATUS USING ION REFLUX

[75] Inventor: Hamish Small, Leland, Mich.

[73] Assignee: Dionex Corporation, Sunnyvale, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/781,537

[22] Filed: Jan. 9, 1997

[51] Int. Cl.$^6$ .................................................. B01D 61/48
[52] U.S. Cl. ........................ 205/789; 204/450; 204/551; 204/600; 204/647
[58] Field of Search .................................... 204/450, 520, 204/536, 551, 600, 632, 647; 205/789, 789.58, 792.5

[56] References Cited

U.S. PATENT DOCUMENTS

| | | | |
|---|---|---|---|
| 3,897,213 | 7/1975 | Stevens et al. | 23/253 |
| 3,920,397 | 11/1975 | Small et al. | 23/230 |
| 3,925,019 | 12/1975 | Small Hamish et al. | 23/230 |
| 3,926,559 | 12/1975 | Stevens | 23/230 |
| 5,045,204 | 9/1991 | Dasgupta et al. | 210/635 |
| 5,569,365 | 10/1996 | Rabin et al. | 204/450 |
| 5,759,405 | 6/1998 | Anderson, Jr. et al. | 210/656 |

*Primary Examiner*—Arun S. Phasge
*Attorney, Agent, or Firm*—David J. Brezner

[57] ABSTRACT

A method and apparatus for generating an acid or base eluent in an aqueous stream solely from an ion exchange bed for liquid chromatography of anions or cations and for simultaneously suppressing conductivity of the eluent in the ion exchange bed after chromatographic separation. For a system in which a base is generated for the analysis of anions by ion chromatography, the method uses a bed of cation exchange material with first and second bed sections arranged in series. For anion analysis, the method includes:

(a) flowing an aqueous feed stream through the first bed section while applying an electrical potential to form an aqueous eluent stream comprising a cation hydroxide base, (b) flowing a liquid sample stream containing anions to be detected and the eluent through a chromatographic separator portion of said first bed section, to separate said anions to be detected, (c) flowing said aqueous separated anion stream through said second bed section substantially free of anion exchange material and including exchangeable hydronium ions, while applying an electrical potential to convert said base to weakly ionized form, and displacing some of said exchangeable hydronium ions with cations from said base, cations electromigrating from said second bed section to said first bed section in the opposite direction to said aqueous feed stream to replenish exchangeable cations displaced from said first bed in step (a), and (d) flowing said suppressor effluent stream past a detector in which the separated anions in said suppressor effluent are detected.

40 Claims, 8 Drawing Sheets

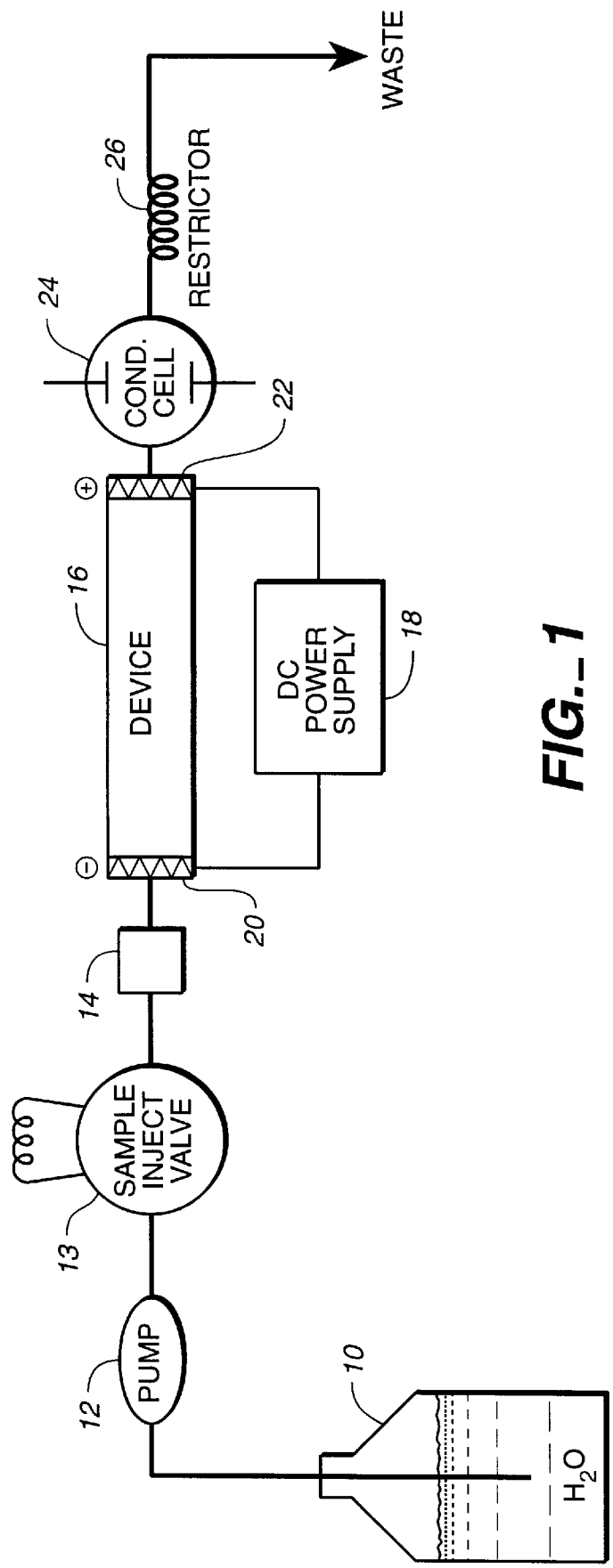
FIG._1

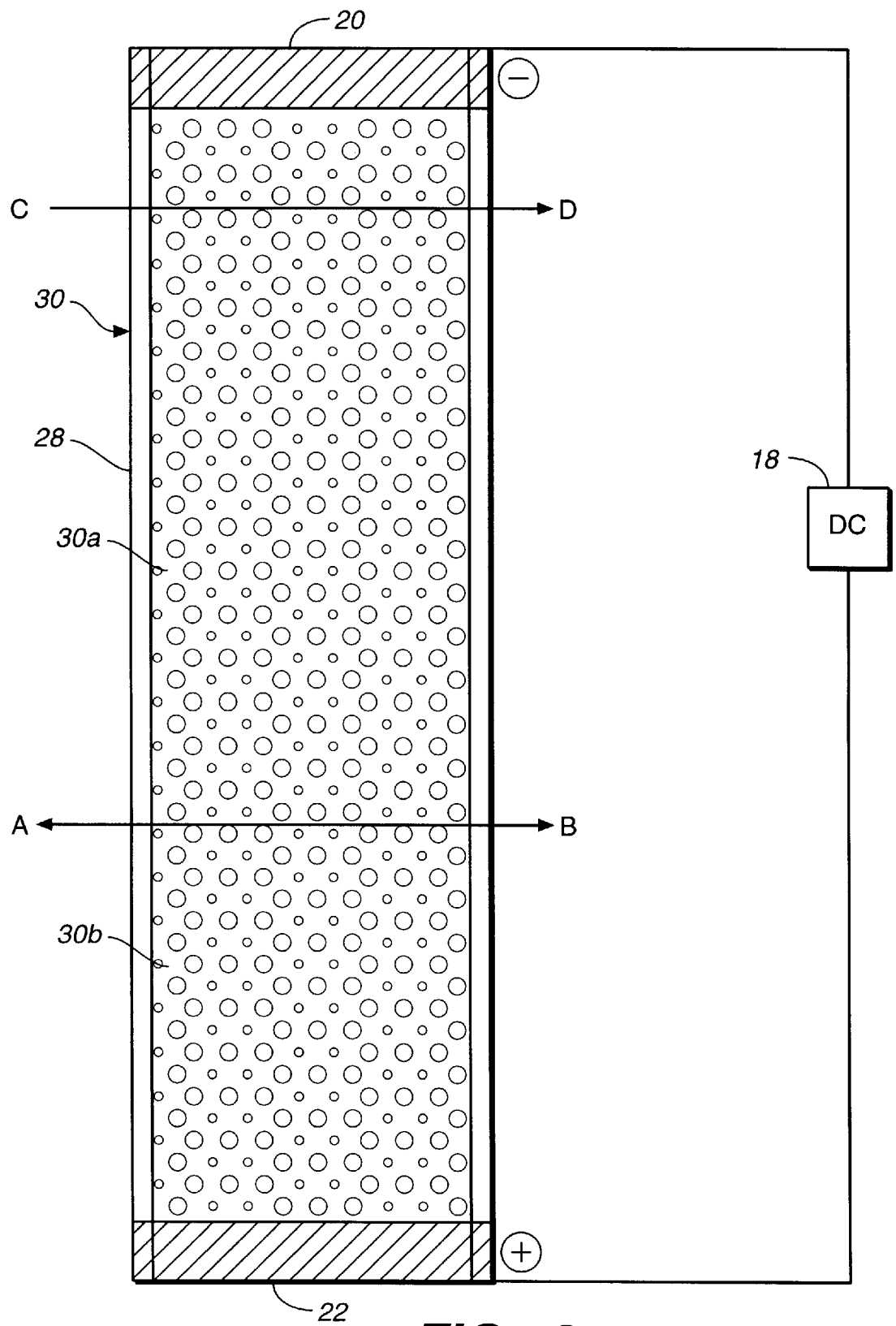
FIG._2

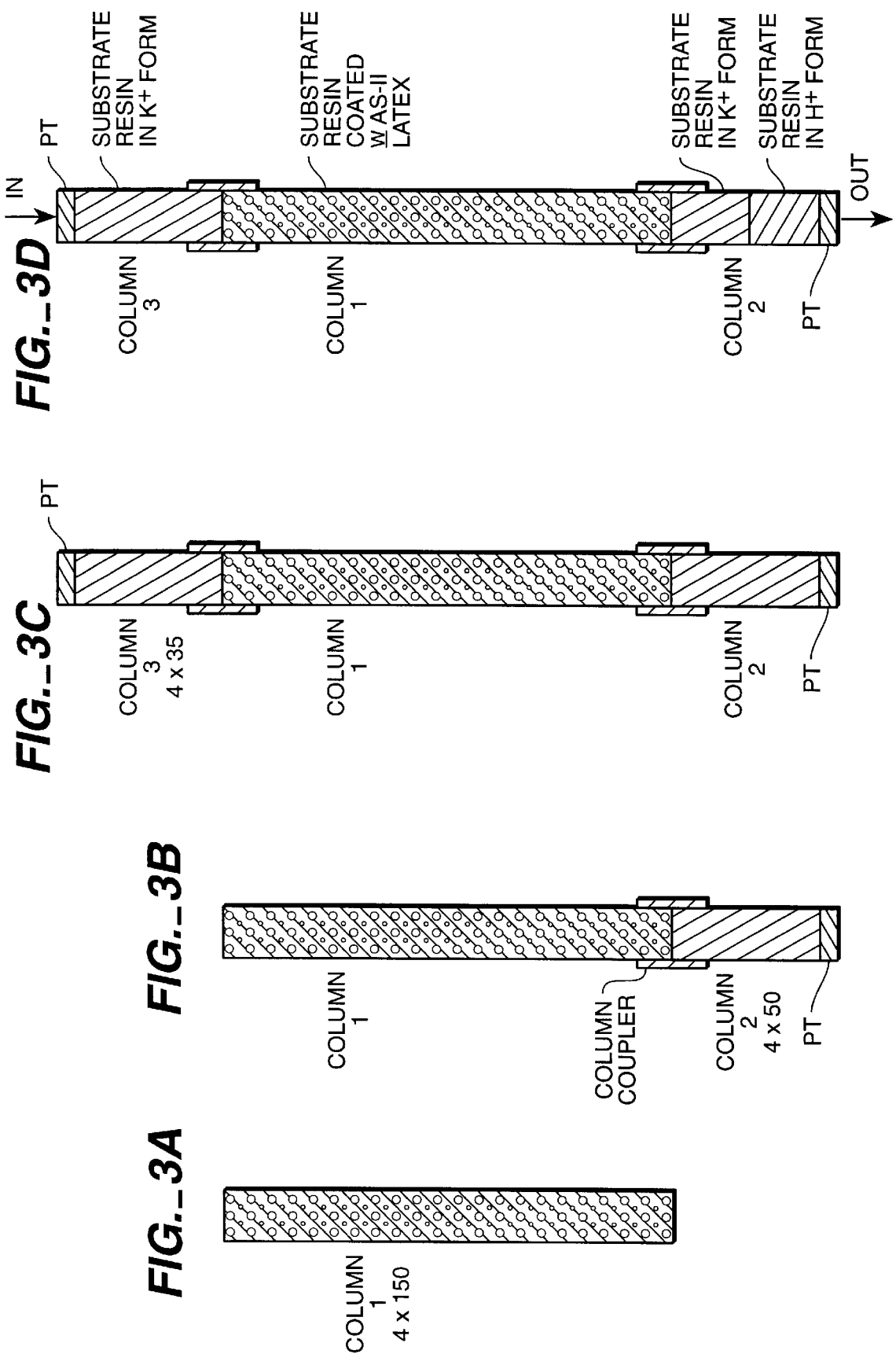

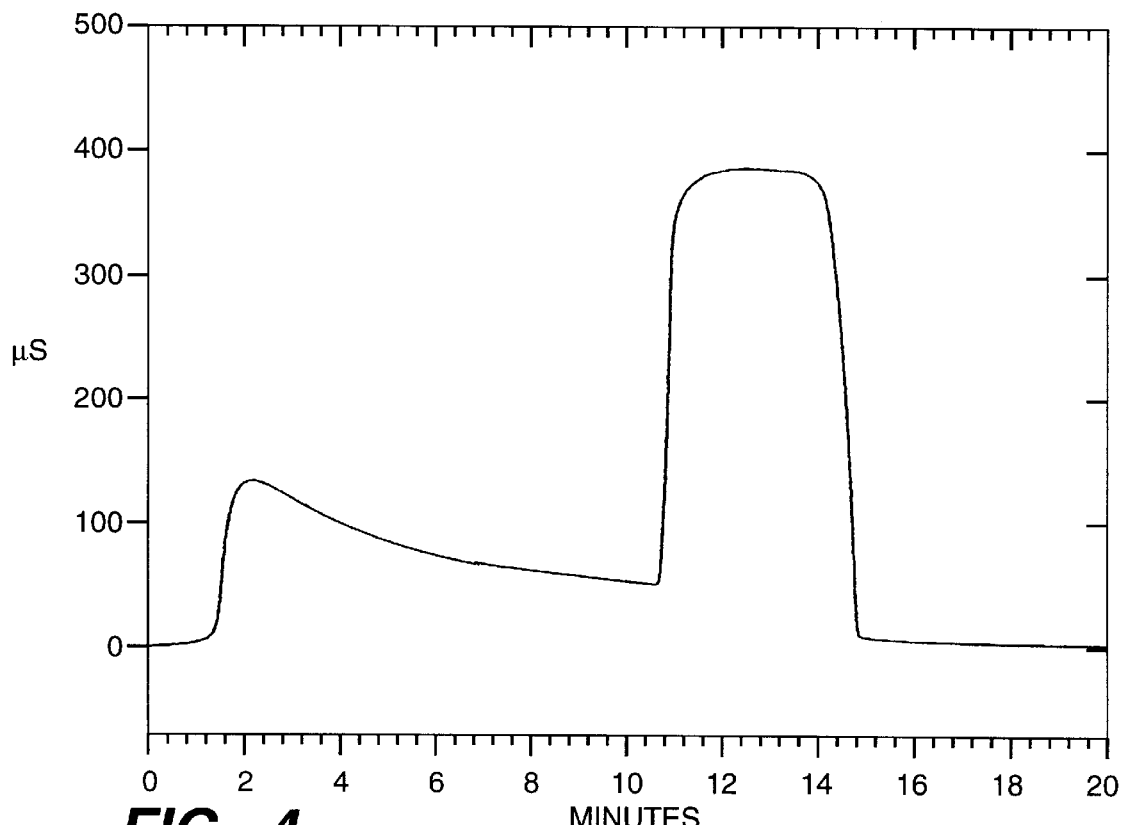
FIG._4
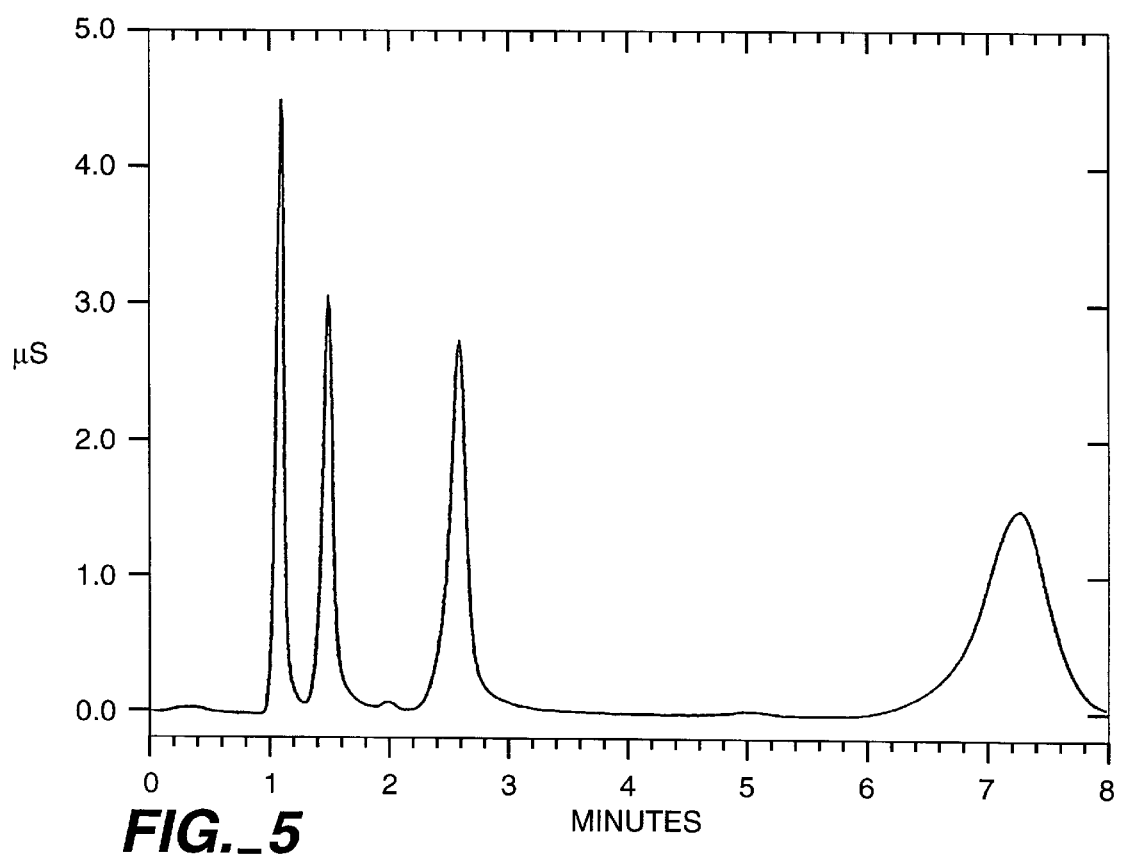
FIG._5

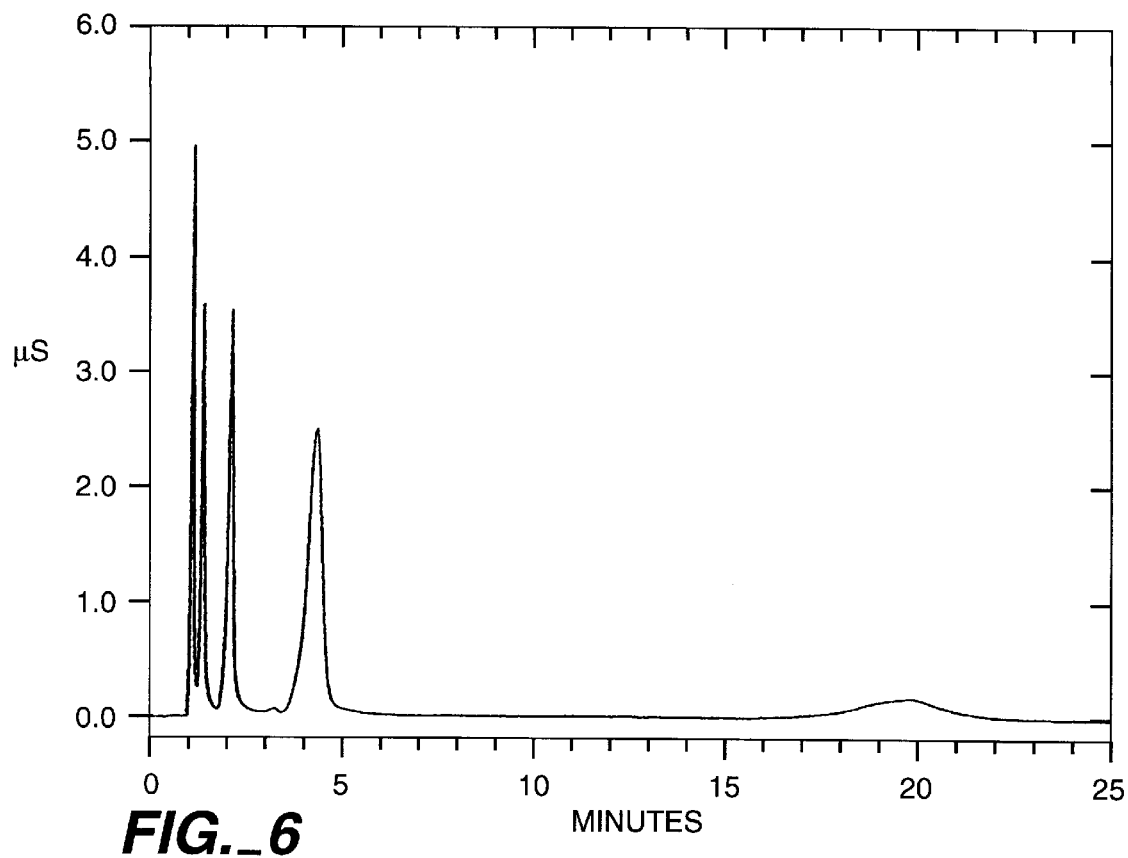
FIG._6
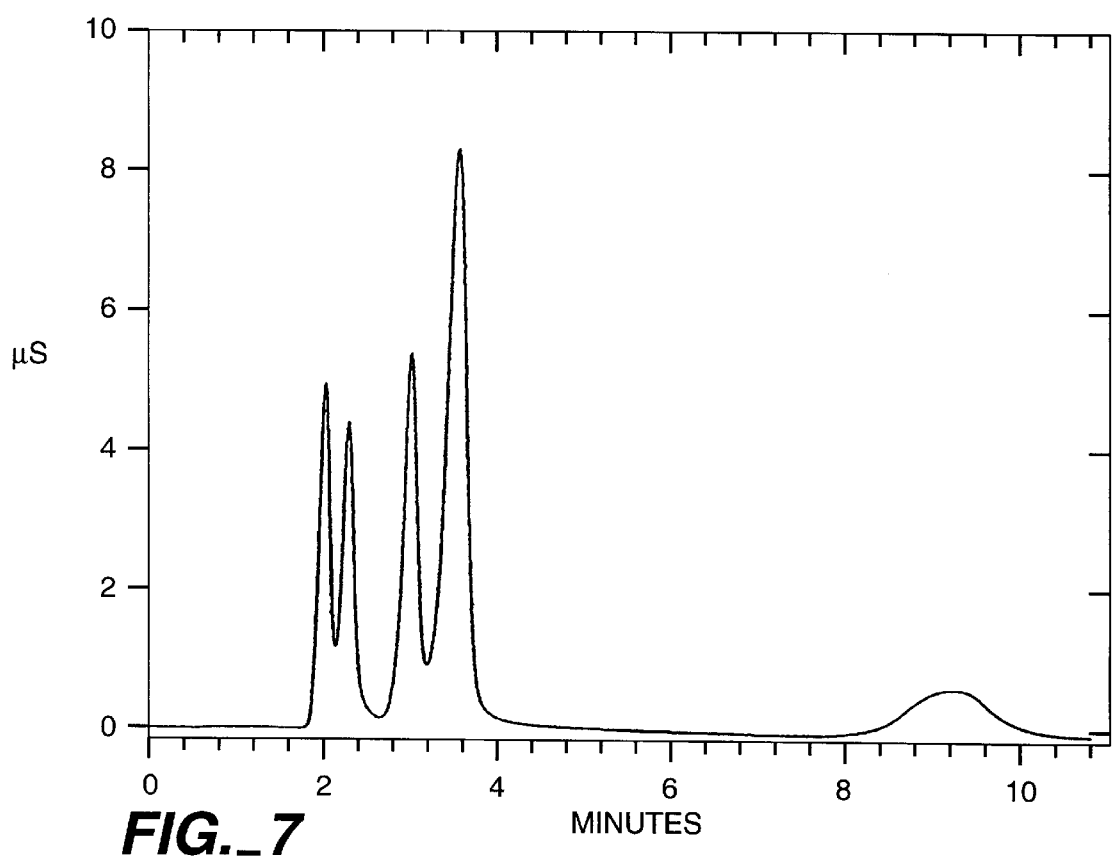
FIG._7

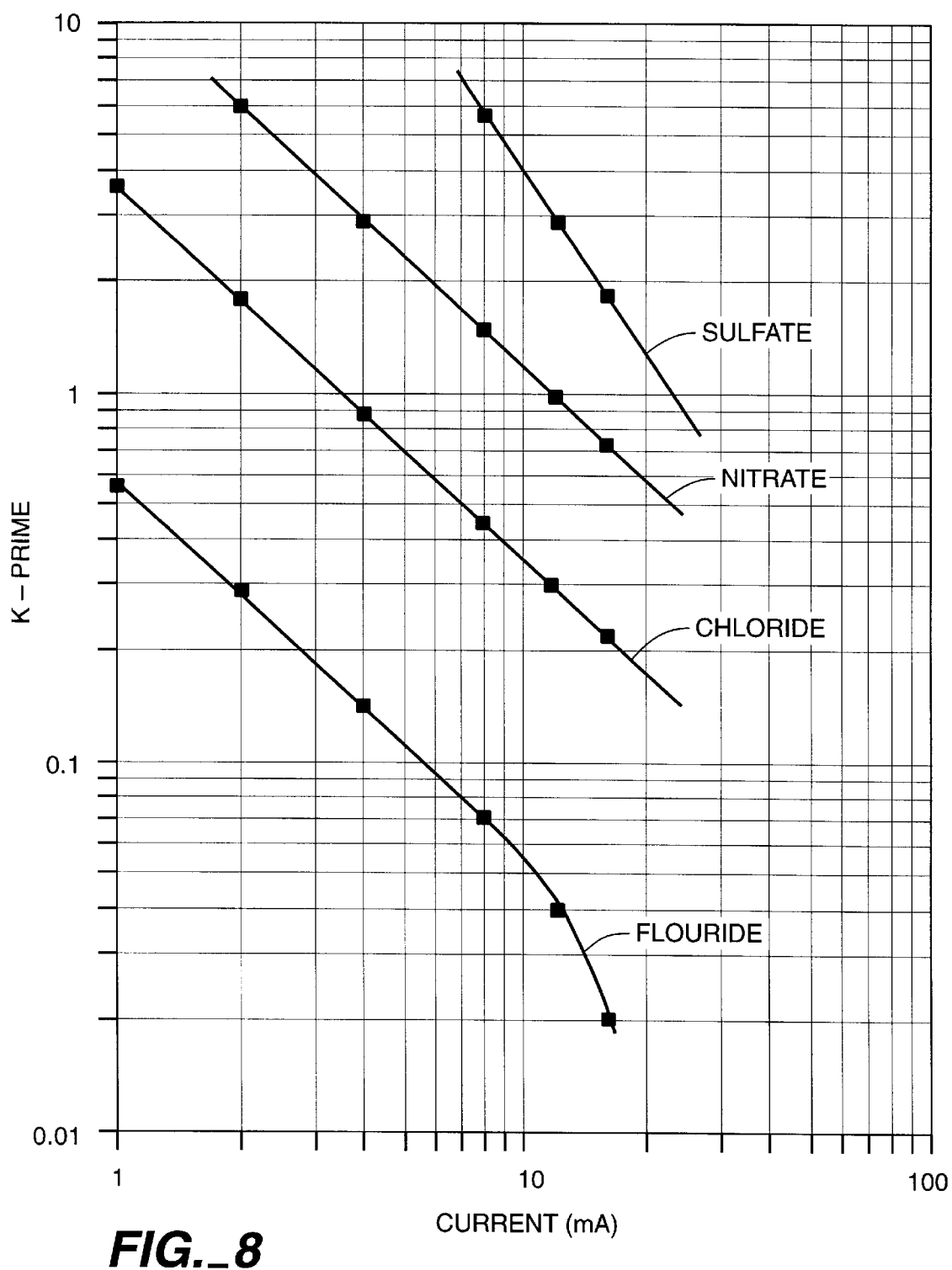
FIG._8

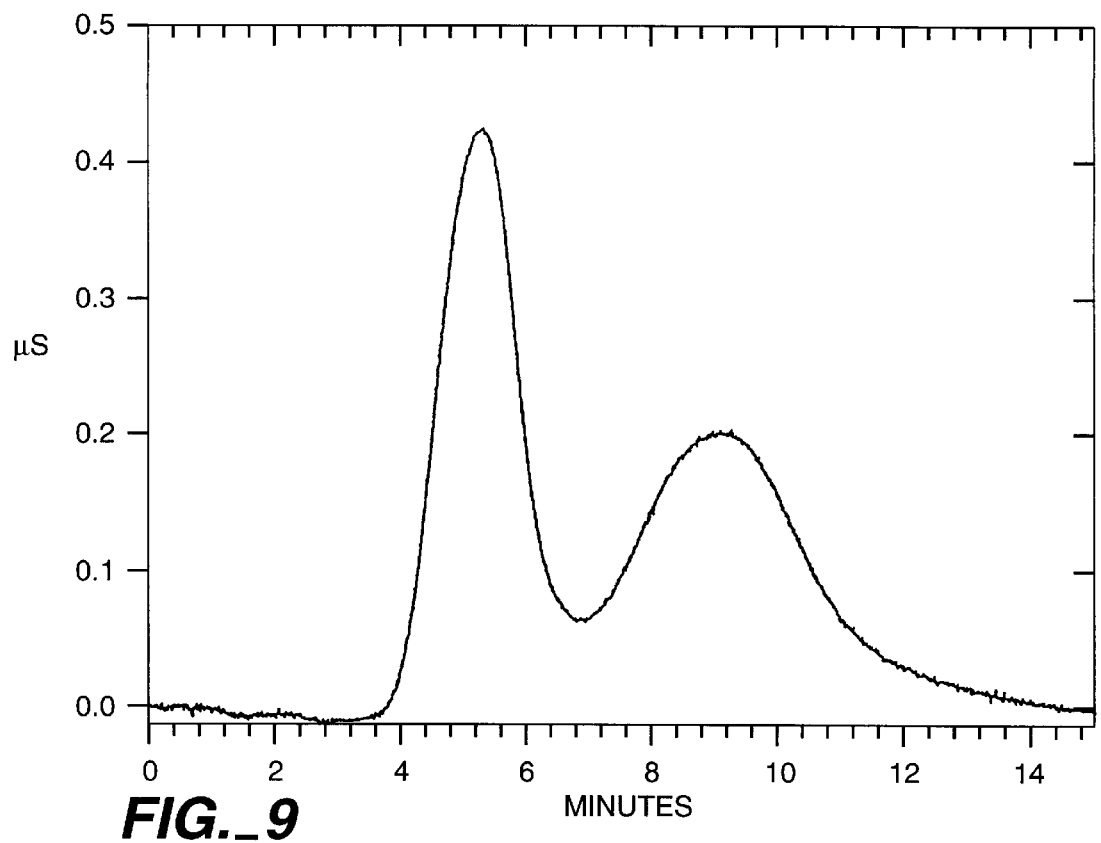
FIG._9
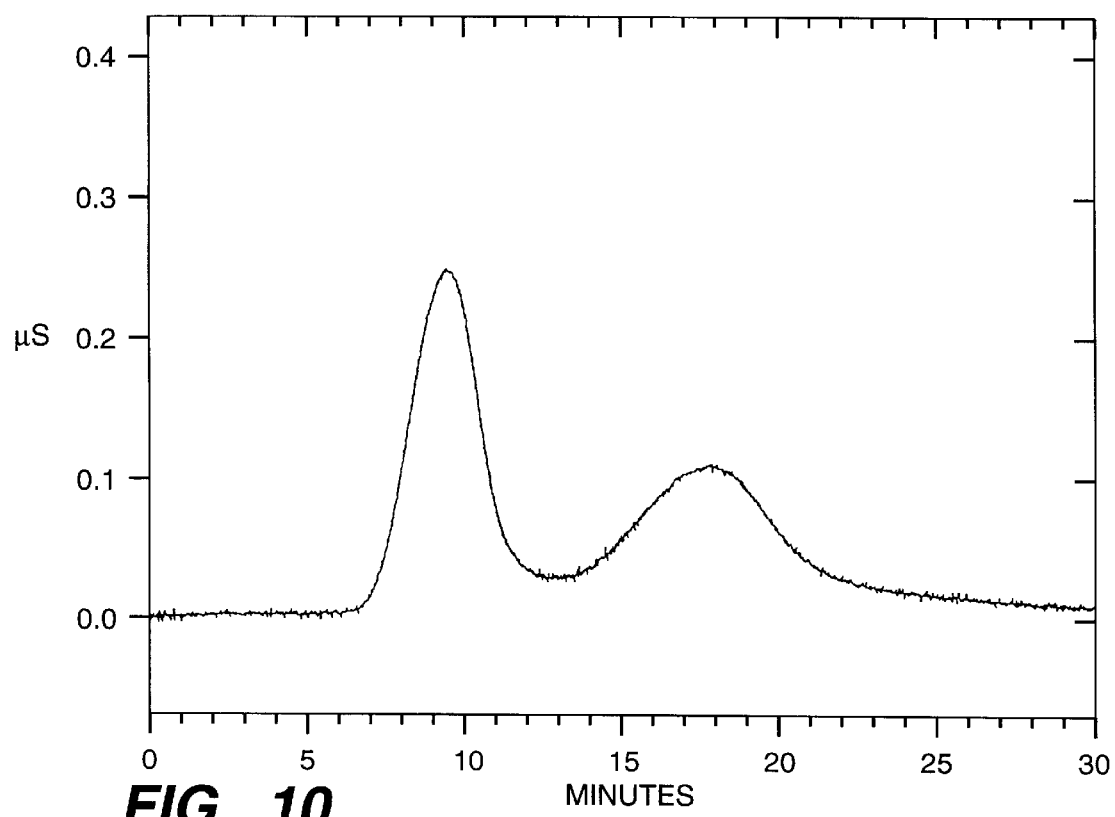
FIG._10

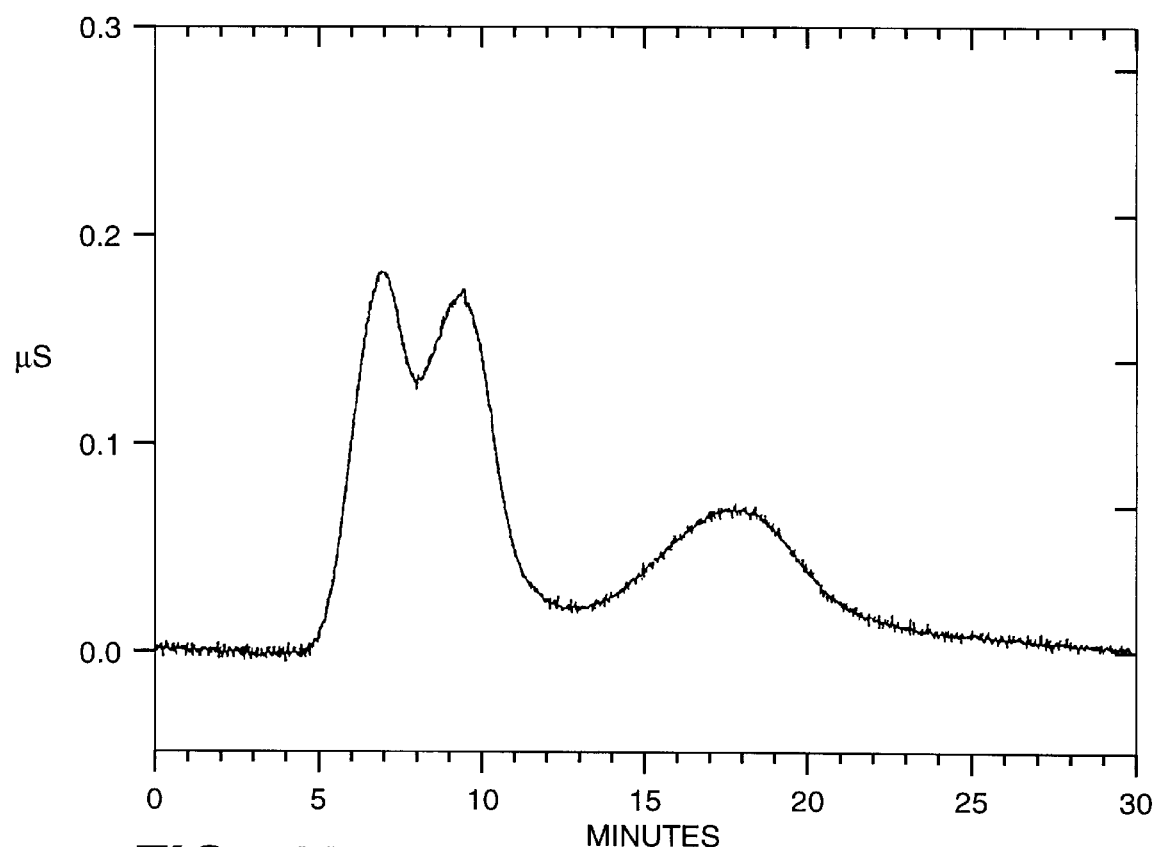
FIG._11

ION CHROMATOGRAPHIC METHOD AND APPARATUS USING ION REFLUX

BACKGROUND OF THE INVENTION

The present invention relates to a method and apparatus for ion chromatography using eluents generated within the system.

In liquid chromatography, a sample containing a number of components to be separated is directed through a chromatography separator, typically an ion exchange resin bed. The components are separated on elution from the bed in a solution of eluent. One effective form of liquid chromatography is referred to as ion chromatography. In this known technique, ions to be detected in a sample solution are directed through the separator using an eluent containing an acid or base and thereafter to a suppressor, followed by detection, typically by an electrical conductivity detector. In the suppressor, the electrical conductivity of the electrolyte is suppressed but not that of the separated ions so the latter may be detected by the conductivity detector. This technique is described in detail in U.S. Pat. Nos. 3,897,213, 3,920,397, 3,925,019 and 3,956,559.

There is a general need for a convenient source of high purity acid or base for use as an eluent for liquid chromatography and, particularly, for ion chromatography. In one technique, described in U.S. Pat. No. 5,045,204, an impure acid or base is purified in an eluent generator while flowing through a source channel along a permselective ion exchange membrane which separates the source channel from a product channel. The membrane allows selective passage of cations or anions. An electrical potential is applied between the source channel and the product channel so that the anions or cations of the acid or base pass from the former to the latter to generate therein a base or acid with electrolytically generated hydroxide ions or hydronium ions, respectively. This system requires an aqueous stream of acid or base as a starting source or reservoir.

There is a particular need in ion chromatography for generating an acid or base internally within an ion exchange bed without the requirement of an aqueous acid or base stream source and for simultaneously suppressing conductivity of the eluent in the ion exchange bed after chromatographic separation.

SUMMARY OF THE INVENTION

In accordance with the present invention, method and apparatus have been provided for generating an acid or base eluent in an aqueous stream solely from an ion exchange bed for liquid chromatography and for simultaneously suppressing conductivity of the eluent in the ion exchange bed after chromatographic separation.

Referring first to a system in which a base is generated for the analysis of anions by ion chromatography, the method uses a bed of cation exchange material including exchangeable cations. The bed has first and second bed sections arranged in series. The method includes the following steps:

(a) flowing an aqueous feed stream through said first bed section while applying an electrical potential to a cathode in electrical communication therewith to generate hydroxide ions in said aqueous stream and assist in displacing some of said exchangeable cations into said aqueous stream to form an aqueous eluent stream comprising a cation hydroxide base, (b) flowing a liquid sample stream containing anions to be detected and said eluent through a chromatographic separator portion of said first bed section, said last named section further comprising anion exchange material, to separate said anions to be detected, (c) flowing said aqueous separated anion stream through said second bed section substantially free of anion exchange material and including exchangeable hydronium ions, while applying an electrical potential to an anode in electrical communication with said second bed and to generate hydronium ions in said separated anion aqueous stream near said anode, to convert said base to weakly ionized form, and displacing some of said exchangeable hydronium ions with cations from said base, said aqueous stream exiting said second section as a suppressed effluent, said first and second bed sections forming a cation path through said cation exchange material between said anode and cathode with said cations electromigrating from said second bed section to said first bed section along said cation path in the opposite direction to said aqueous feed stream to replenish exchangeable cations displaced from said first bed in step (a), and (d) flowing said suppressor effluent stream past a detector in which the separated anions in said suppressor effluent are detected.

For anion analysis, the apparatus includes the following components:

(a) a sample injection port (b) a flow-through bed of cation exchange material including exchangeable cations, said bed having first and second bed sections arranged in series, said first bed section being in fluid communication with said sample injection port, said first bed section further comprising a chromatographic separator portion including anion exchange material capable of separating anions in an aqueous sample stream flowing through said chromatographic separator portion, said second bed portion being substantially free of anion exchange material and being capable of converting base following in an aqueous stream therethrough into weakly ionized form, (c) first and second electrodes in electrical communication with said first and second bed sections, respectively, the cation exchange material in said first and second bed sections forming a cation path through said cation exchange material between said first and second electrodes, and (d) a power supply for applying a potential between said first and second electrodes.

The cation exchange bed may be in the form of a packed bed of cation exchange resin particles or some other form as described herein. The chromatographic separator portion of the bed may be formed of such cation exchange resin particles coated with fine anion exchange resin particles. Such coated particles are known as agglomerated resin as used as a separator column in conventional ion chromatography, but for this invention the substrate cation exchange particles are preferably of high capacity. However, substrate cation exchange resin of lower capacity (e.g., less than 0.5 meq/mL) may be used as long as the substrate resin forms a conductive ion bridge of efficient transfer of exchangeable cations.

Since hydrogen and oxygen gases are generated in the ion exchange bed which could interfere with detection, it is preferable to pressurize the chromatographic effluent prior to detection, such as by use of a flow restrictor.

The above system has been described for anion analysis. However, it is also applicable to cation analysis by appropriate reversals of the cation and anion analysis functions.

BRIEF DESCRIPTION OF THE DRAWINGS

FIG. 1 illustrates the device of the present invention in an ion chromatography system.

FIG. 2 is a schematic expanded cross-sectional view of the device of the present invention.

FIGS. 3A–3D are schematic views of components used in manufacturing the device of the present invention.

FIG. 5 is a graph showing effluent conductance as a function of time.

FIGS. 4–7 and 9–11 are chromatograms illustrating the present invention.

FIG. 8 is a plot of k-prime vs. current illustrating the present invention.

DETAILED DESCRIPTION OF THE PREFERRED EMBODIMENTS

The method and apparatus of the present invention first will be described with respect to anion analysis and using an ion exchange resin packed bed form of ion exchange bed. Referring specifically to FIG. 1, a simplified ion chromatography apparatus is illustrated. The system includes a source of an aqueous stream such as deionized water reservoir 10 which is pumped through sample injector valve 13 and optional cation stripper column 14, to a flow-through bed of cation exchange material in device 16 which serves the functions of (1) base generation, (2) separation or resolving of the anions, and (3) suppression of the generated base after separation. A DC power supply 18 is connected to electrodes 20 and 22, with a polarity so that as the former is a cathode and the latter is an anode. Preferably the power supply includes a variable output potential. A suitable power supply is a Pharmacia Biotech Electrophoresis power supply EPS 600 model.

The effluent from device 16 is directed through a flow-through conductivity cell 24 for detecting the resolved ions in the effluent from column 16. A suitable data system, not shown, is provided in the form of a conventional conductivity detector for measuring the suppressor effluent in conductivity cell 24. In conductivity cell 24, the presence of ionic species produces an electrical signal proportional to the amount of ionic material. Such signal is typically directed from cell 24 to a conductivity meter (not shown) forming part of a data system permitting direct detection of the concentration of the separated ionic species. Other detectors may be used including a pulsed amperometric detector and a UV visible detector. With the exception of columns 14 and 16, such ion chromatography systems are well known, e.g. as illustrated in U.S. Pat. Nos. 3,897,213, 3,920,397, 3,925,019 and 3,956,559.

The system also includes means for pressurizing the effluent from device 16 prior to detection to minimize adverse effects of gases hydrogen and oxygen) generated in device 16 as will be described hereinafter. As illustrated in FIG. 1, such pressurizing means comprises a flow restrictor 26 downstream of conductivity cell 24 to maintain the ion chromatography system under pressure.

FIG. 2 illustrates device 16 in more detail. Device 16 is typically in the form of a hollow cylindrical column 28 containing a cation exchange bed 30 extending the entire distance from cathode 20 to anode 22. Column 28 is shown schematically, and so is not illustrated with its top and bottom walls or with the inlet and outlet liquid couplings which could be of a conventional type used for packed bed suppressor columns or chromatography separator columns such as sold by Dionex Corporation. Column 28 may be assembled from a single column or use separate columns coupled together as described in the examples.

The illustrated electrodes 20 and 22 are suitably in the form of porous metal disks (e.g. platinum) at the inlet and outlet respectively of the column, serving as supports holding the resin particles of the packed bed in close contact. If desired, the electrodes can be placed elsewhere in contact with the resin particles close to the inlet and outlet to bed 30 (e.g. within 5 to 10% of the inlet and outlet respectively). Also, the electrodes may take forms other than porous disks (e.g. rings, screens or probes) so long as they provide good contact with the ion exchange bed.

As used herein, the terms "anion or cation or ion exchange beds" refer to flow-through beds of ion exchange material through which the aqueous stream flows. Unless otherwise stated, the term "cation" excludes hydronium ion and the term "anion" excludes hydroxide ion. Because of its ready availability and known characteristics, a preferred form of ion exchange bed is a packed ion exchange resin bed. It is important that the resin particles be tightly packed in the bed, to form a continuous ion bridge or pathway for the flow of anions or cations between the electrodes in the opposite direction to flow of the aqueous stream. Also, there must be sufficient spacing for the aqueous stream to flow through the bed without undue pressure drops.

In the present system as will be described below, the sole source for a reservoir of cations for generating the bases is the cation exchange bed. This is to be contrasted with the eluent generator of U.S. Pat. No. 5,045,204 in which the reservoir of the acid or base is a preexisting aqueous stream of acid or base which provides the cations or anions which pass transversely through the membrane into the eluent product flow stream. In the present invention, the source of cations or anions is the ion exchange bed and the acid or base is generated during the flow of the aqueous stream through the bed. The present cation exchange bed extends in a network transverse to the flowing aqueous stream and provides a continuous electrical path for cations in contact with both the anode and the cathode. Thus, the definition of ion exchange bed excludes a membrane suppressor structure.

Cation exchange bed 30 includes a first bed section 30a above, i.e., to the inlet or cathode side of line A–B and a second bed section 30b below, i.e., to the outlet or anode side of the column. As illustrated in FIG. 2, the cation exchange material in the first and bed sections 30a and 30b are contiguous or in direct contact with each other. It is important that the two bed sections form a continuous cation path through the cation exchange material between the anode and cathode. However, this could also be accomplished by placing other flow-through cation conductive material, such as a cation conductive screen, between the two ion exchange bed sections, if desired for some purpose.

In bed section 30a, the base for the eluent is generated and the anions are separated. In the illustrated embodiment, bed section 30a itself includes two different types of cation exchange material. Above line C–D is an ion exchange material substantially free of anion exchange material. In this embodiment, the cation exchange material in this portion of bed section 30a may be in the form of conventional high capacity exchange resin of sufficient capacity to provide the desired concentration of base for anion separation. Suitably, high capacity ion exchange resins are typically in the capacity range of from a minimum of about 0.5 to as high as 3 milliequivalents per ml. or more. Suitable cation exchange resins have moderate to high cross-linking (e.g. sulfonated polystyrene/divinylbenzene resin with about 4% to 20% cross-linking). However, ion exchange resins with ion exchange capacity less than 0.5 meq/mL may be used as long as there is an efficient transfer of the exchangeable cations from bed section 30b through bed section 30a to the region of electrode 30.

The exchangeable cations or anions must also be sufficiently water soluble in base or acid form to be used at the desired concentrations. Suitable cations are metals, preferably alkali metals such as sodium, potassium, lithium and cesium. Known packing for high capacity ion exchange resin beds are suitable for this purpose. Typically, the resin support particles may be in the potassium or sodium form. Potassium is a particularly effective exchangeable cation because of its high conductance. Suitable other cations are tetramethyl ammonium and tetraethyl ammonium. Analogously, suitable exchangeable anions for cation analysis include chloride, sulfate and methane sulfonate. Typically, resin support particles for these exchangeable anions include Dowex 1 and Dowex 2.

Other forms of ion exchange beds can be used such as a porous continuous structure with sufficient porosity to permit flow of an aqueous stream at a sufficient rate for use as an eluent for chromatography without undue pressure drop and with sufficient ion exchange capacity to form a conductive bridge of cations or anions between the electrodes. One form of structure is a porous matrix or a sponge-like material formed of sulfonated, cross-linked polystyrene with a porosity of about 10 to 15% permitting a flow rate of about 0.1 to 3 ml/min. without excessive pressure drop. Another suitable form is a roll of ion exchange film (e.g. in a configuration of a roll of ion exchange film on a spindle disposed parallel to liquid flow). Electrodes would be placed at each end of the roll. The film could be textured to provide an adequate void channel.

High purity (deionized) water is pumped to the inlet region of section 30a, in an accurate and controllable flow rate by a typical high pressure chromatography pump. Base is generated while water is flowing in this region by the application of a DC potential to porous inert metals disk cathode 20. Water is split at both cathode 20 and anode 22. The cathode reaction in the upstream portion of bed section 30a produces hydroxide ions in the following cathodic reaction.

$$2H_2O + 2e^- \rightarrow 2OH^- + H_2 \qquad (1)$$

As will be explained below at the anode of the exit of bed 30 in bed section 30b, hydronium ions are produced according to the following anodic reaction.

$$H_2O - 2e^- \rightarrow 2H^+ + \tfrac{1}{2}O_2 \qquad (2)$$

The aqueous feed stream flows past cathode 20 into the inlet or upper region of bed section 30a while an electrical potential is applied to the cathode which generates hydroxide ions in the foregoing manner. At the same time, some of the exchangeable cations on the bed cation exchange material (preferable cation ion exchange resin) are displaced into the aqueous stream to combine with the thus formed hydroxide ions to form a cation hydroxide base serving as the aqueous eluent steam for performing the anion separation. As will be described below, bed section 30a includes an anion separator portion comprising anion exchange material. In one embodiment, this separator portion of bed section 30a constitutes the entire bed section 30a and there is no difference between the packing above and below line C–D. This is possible because it has been found that generation of the base will also occur in the presence of the anion exchange material in the chromatographic separator region.

The aqueous stream in source 10 may be high purity deionized water. However, for some forms of chromatography, and particularly ion chromatography, it may be desirable to modify the source with an additive which reacts with the base generated at the cathode to produce eluents of varying potency. For the production of a base, such well known additives include a source of carbonic or boric acid, phenol, cyanophenol, and the like. For the production of acid, such additives include m-phenylene diamine, pyridine, lysine, and amino propionic acid.

The aqueous stream is pumped at rates determined by the analytical process to be used. For ion chromatography, typical flow rates of 0.1 to 3 ml/min are employed.

The chromatographic separator portion of bed section 30a, which may comprise the entire bed section 30a, includes anion exchange material. One preferred form of said separator section is the use of conventional agglomerated resin particles used in packed separator beds in ion chromatography. Such conventional agglomerated separator resins are fully described in U.S. Pat. Nos. 4,101,460, 4,252,644, and 4,519,905.

Briefly summarized, such patents describe "agglomerates" of cation substrate support particles coated with fine layering anion exchange resin particles (e.g. deposited from a latex). The anionic layering particles are retained by electrostatic forces with the oppositely charged cationic support particles. Such conventional separator resins were developed for the purpose of providing a low capacity separator column to be used in conjunction with a high capacity suppressor, thereby avoiding frequent regeneration of the suppressor. Other types of agglomerated resin may be made such as by grafting or the like so long as the exchangeable anions retain their ability to separate the sample anions and the cation substrate support particles retain their ability to transport cations in a path through the resin bed.

Suitable cations substrate resins for the agglomerates have the same high capacity as described above for the high capacity cation exchange material for generating the base at the cathode. However, cation substrate resins of lower ion exchange capacity (e.g., less than 0.5 meq/mL) may be used as long as the substrate resin forms a conductive ion bridge for efficient transfer of exchangeable cations. Suitable capacities for the latex coating or layering particles typically are about 0.1 to 2 meqs/ml.

Forms of the cation exchange material other than packed resin beds (e.g. the sponge-like bed or rolls described above) may be used as the support for the anion exchange material. Here, the anion exchange material takes the form of the same type of latex and is retained the same way, by the cation exchange material.

In the chromatographic separator portion of bed section 30a, the anions in the aqueous sample stream are separated in a conventional manner as set forth in the above patents. Thereafter, the aqueous stream including the base eluent and separated anions flow into section 30b which serves as a suppressor and also provides cations to replenish the exchangeable cations displaced from the cation exchange material during generation of the base in section 30a as will be described below.

Bed section 30b is filled with ion exchange material preferably in the form of high capacity cation exchange resin particles similar to the type used in a conventional packed bed suppressor column described in the U.S. Pat. Nos. 3,897,213, 3,920,397, 3,925,019 and 3,956,559. As will be described, there is a constant recycle of cations along the cation exchange resin particles. The same type and capacities of cation exchange resin may be used in bed sections 30b and as the support particles for the agglomerated resin in section 30a. However, different types of cation exchange resin may be used in these two sections so long as there is a efficient transfer of the exchangeable cations from bed section 30b through bed section 30a to the region of cathode 20.

In the upper end of bed section 30b, base is suppressed as in a conventional packed bed suppressor. Thus, the cation of the cation hydroxide base displaces hydronium ions on the ion exchange bed to convert the base into weakly ionized form. If the aqueous stream is pure water, the weakly ionized form is water. If the aqueous stream includes a weak acid, the weakly ionized form is that weak acid, as in conventional suppression.

At the region of bed section 30b near the anode, hydronium ions are generated which displace exchangeable cations on the cation exchange material which, during suppression, had conversely displaced hydronium ions on the column. The cations electromigrate in a cation path along the cation exchange material (e.g. cation exchange resin) in the direction opposite to the aqueous liquid stream flow from bed section 30b to bed section 30a and back to cathode 20.

As an overview, cation hydroxide produced at the cathode is carried by the aqueous stream into the separator portion of the bed to serve as the eluent for separation. During suppression, cations displace the exchangeable hydronium ion on the cation exchange material where the cations are carried back to replace the cations lost at the entrance to the column in the region adjacent the cathode to permit the continuous generation of cation hydroxide. In essence, the cations are "refluxed" through the system to provide a steady state in which the boundary in bed 30b between hydronium and cation form remains substantially spatially fixed (e.g. a variance of less than about 5% of the total length of bed 30). For example, if the current is increased, the flux of hydronium ions correspondingly increases in the direction of the cathode. This should cause an exact equivalence in the amount of base produced at the cathode to increase the concentration of base flowing in the opposite direction to just balance the increased flux of hydronium ions thereby retaining the boundary in the same fixed position. This overall movement of cation in one direction and return in a continuous contiguous aqueous phase in the opposite direction is analogous to the reflux of distillation.

The above reflux system provides for substantially perpetual regeneration of the base for use as the eluent. The only reason that it would not be totally perpetual is that the cations in salts of the anion sample stream eventually would consume the suppressor portion of the device. This impediment to perpetual reflux is overcome by the removal of the cations in the aqueous sample stream. A convenient way to do this is to pretreat the aqueous liquid sample stream by flowing through hydronium ion exchange stripper bed 14 prior to flow into column 16 to convert sample salts to their acid form. Bed 14 should have a high capacity similar to a conventional packed bed suppressor (e.g. 1 to 2 milliequivalents/ml.) so that it may be regenerated or periodically replaced but only after a long interval of use (e.g. on the order of 100 to 1000 samples).

The volume (length) and/or capacity of bed section 30a will be determined mainly by the length of separator bed deemed necessary to provide adequate separations for a wide variety of analyte mixtures; this length might typically be 25 cm. Section 30b on the other hand preferably is the minimum length necessary to provide efficient suppression; this length (e.g. 5 cm) typically is substantially less than that of section 30(a).

It is preferable to tightly pack the ion exchange material, particularly in the form of resin so that a continuous ion conducting path is formed through the resin particles and contact the two electrodes. The aqueous liquid may push the ion exchange particles away from electrode 20 at the entrance to column 28. Thus, it is preferable to counteract this tendency to separate. A physical spring could be loaded at the entrance of column 28 to push the cathode 20 against the resin. Alternatively, a "resin-spring" may be formed for this purpose. That is, a resin is placed at the entrance section has a tendency to push out against this electrode and oppose the water flow compression effect. This can be accomplished by a shrink-swell procedure on the Dowex 50W resin as illustrated in the Examples.

It is preferable to maintain a constant concentration of acid (or base). To do so, the current which is directly related to concentration should also be constant. A feedback loop may be provided to assure sufficient voltage to deliver the predetermined, constant current (e.g. 5–10 milliamps). Thus, the current is monitored and when the resistance changes, the potential is correspondingly changed by the feedback loop. Therefore, the voltage is a slave to the reading of the current. Thus, it is preferable to supply a variable output potential system of this type (e.g. one sold under the designation Electrophoresis Power Supply EPS 600 by Pharmacia Biotech.

The electrode reactions produce electrolysis gases, hydrogen and oxygen, which are carried forward into the chromatography system. If these gases are produced in significant volume relative to the liquid flow, their presence can be detrimental to chromatographic efficiency. This potential problem can be eliminated by application of Boyle's law. Specifically, the system can be operated at an elevated pressure (e.g. 100 to 1500 psi ) so that the gases are compressed to a volume that is insignificant compared to the flow of the aqueous liquid stream. The pressure necessary to accomplish this depends on the volume of gasses produced. However, for a typical system, a pressure of at least 250 to 500 psi is sufficient. One mode of elevating the pressure is to connect a flow restrictor such as a fine bore coiled tubing 26 downstream of the detector (e.g. three meters of 0.005 in I.D.). This elevates the pressure throughout the chromatography system upstream of the detector. In the present system, it is preferable to construct the conductivity cell to be capable of withstanding a pressure of 1500 psi or more above ambient pressure. A lower pressure of 250 to 500 psi could be used under most conditions. Such system pressure may be high enough to interfere with effective use of membrane suppressors.

The ion chromatography system of the present invention has been described with respect to the separation of anions using a perpetually regenerated base. It is also applicable to the generation of an acid for cation analysis with appropriate modification of the cation exchange bed to an anion ion exchange bed in a reversal of polarities. The reactions at the cathode and anode are illustrated in equations (1) and (2) above, respectively. Here the exchangeable anion (e.g. chloride) is electromigrated at the entrance of the bed into the aqueous stream where it combines with hydronium ions formed there by the splitting of water to form the acid eluent. At the other end of the bed, hydroxide ions electromigrate onto the bed and the anions move in a continuous anion path along the resin particles back towards the anode to continuously replenish anions the lost to generate the acid.

In order to illustrate the present invention, the following examples are provided.

EXAMPLE 1

Preparation of a Column for Anion Analysis

Although an entire device can be assembled within a single plastic column, the device described here used three separate columns coupled together.

Column 1 in FIG. 3A (the separator portion of bed section 30a) was a 4×150 mm PEEK column. This was equipped with a bed support and filled with the potassium form of a strong cation exchange resin of particle size about 20 micrometers and nominally 8% cross-linking. This resin was then treated by pumping slowly through it a dilute suspension, in water, of an anion exchanging latex resin (Dionex AS-11 latex). This procedure deposits a monolayer of colloidal anion exchanger on the substrate resin and the composite surface agglomerated resin becomes the separating material for the IC process. This step was followed by a thorough water rinse to displace any unattached latex from this bed.

Column 2 in FIG. 3B which eventually contained the suppressor section (bed section 30b) was a 4×50 mm PEEK column. This column was coupled directly to what would eventually be the outlet end of bed section 30a and filled with the same cation exchange resin as bed section 30a, also in the potassium form. The outlet of bed section 30b of column of FIG. 3B was then equipped with a porous Pt electrode/bed support. At this point the assembly can be represented by FIG. 3B.

Column 3 of FIG. 3C was a 4×35 mm PEEK column. This column was equipped with a porous Pt disc bed support and packed with of Dowex 50W X 4 potassium form which had previously equilibrated with 20% potassium nitrate to shrink the resin. This resin filled column was in turn coupled to the inlet of Column 1. The complete assembly at this point is represented by FIG. 3C.

At this stage the complete assembly was treated by pumping deionized water in the direction shown by the arrow in FIG. 3C. The purpose of this step is to re-swell the Dowex 50 W in the entrance section.

The final step in preparing a device for use is to convert some of the resin in column 2 to the hydronium form. This was done by pumping 0.01M nitric acid at 1 ml/min. in the direction of the arrows in FIG. 3C. The amount of acid pumped was precisely controlled; in this instance 40 ml. of acid was pumped and followed by a water wash which means that 0.4 milliequivalents of suppressor capacity has been implanted at the exit end of the device. The complete assembly at this point was as represented in FIG. 3D. The device was now ready for testing.

EXAMPLE 2

In this Example, the column built according to Example 1 was conditioned for ion chromatography. Prior to use, it was washed free of nitrate ions deposited on the separator resin during nitric acid treatment that implanted suppressor capacity on the lower section of the column. This was done by polarizing the bed as would be used in operation while pumping water through it. FIG. 4 shows a history of the effluent conductance as a function of time of flow. Here, the DC potential was applied after about 7 minutes after water flow. The broad band of conductance starting at about 11 minutes and ending at about 15 minutes represents the displacement of nitrate ions by hydroxide and conversion to nitric acid in the suppressor column. When the conductance drops to its final level, the system is ready for use.

EXAMPLE 3

FIG. 5 shows the chromatogram obtained on injecting a mixture of four anions while the device of Example 2 was polarized to give a constant current of 8 mA. The flow rate of water to the bed was 1 ml/min.

EXAMPLE 4

FIG. 6 is the chromatogram for five anions injected while the device of Example 2 was polarized to a constant current of 12 mA. The flow rate of water in this case was also 1 ml/min.

EXAMPLE 5

FIG. 7 is the chromatogram for five anions injected while the device was polarized to a constant current of 12 mA but the flow rate of water was reduced to 0.5 ml/min.

In this instance the concentration of KOH generated at the entrance electrode is twice what it was in Example 2 which explains the more rapid elution of the polyvalent ions sulfate and phosphate.

The Table is a summary of the elution behavior of several ions of this device at various conditions of constant current. This data, in conjunction with the Examples, illustrate an important feature of the invention viz. the ability to control chromatographic behavior simply by altering the potential and/or the water flow applied to the device. The data is also plotted in FIG. 8.

Elution times (minutes) for various analyte anions on the device at various currents

| Current mA | Fluoride | Chloride | Nitrate | Sulfate |
|---|---|---|---|---|
| 1 | 1.53 | 4.6 | | |
| 2 | 1.27 | 2.78 | 7.0 | |
| 4 | 1.12 | 1.85 | 3.83 | |
| 8 | 1.05 | 1.43 | 2.45 | 6.65 |
| 12 | 1.02 | 1.28 | 1.95 | 3.92 |
| 16 | 1.00 | 1.20 | 1.70 | 2.83 |

EXAMPLE 6

Preparing the Cation Exchange Resins

Quantities of Dowex 2X8, 200–400 mesh and Dowex 2X8, 2000–400 mesh and Dowex 1X4, 200–400 mesh, all in the chloride form, were converted to their respective hydroxide forms by treating them with a copious excess of 1 normal sodium hydroxide. The resins were then converted to the methane sulfonate form by neutralizing the hydroxide form resins with methane sulfonic acid (NSA).

EXAMPLE 7

Assembling and Testing a Working Cation Exchange Device

As in the of the device described in the foregoing Examples for anion analysis, the device for cation analysis was assembled by coupling three separate columns A, B, and C with analogous but reversed functions.

Column A (the separator section of bed section 30a) was a 4×150 mm PEEK column. This was equipped with a bed support and filled with Dowex 1X8 MSA form. This resin was then treated by passing slowly through it (manually with a syringe) a dilute suspension of a Dionex CS3 cation exchange latex until some time after latex had appeared in the effluent.

This section was then tested in a conventional manner to measure its ability to separate cations. A methane sulfonic acid generator was the source of the eluting acid.

Column B which eventually contained bed section 30b (the suppressor section) was a 4×50 mm PEEK column. This column was coupled directly to what would eventually be the outlet end of column A and filled with Dowex 2X8, 200–400 mesh, MSA form. The outlet of column B was then equipped with a porous platinum electrode/bed support.

Column C was a 4×35 mm PEEK column. This column was equipped with a porous platinum bed support and filled with Dowex 1X4, 200–400 mesh, MSA form which had previously equilibrated with 1 molar methane sulfonic acid. The filling fluid in the preparation of this column was also 1 molar methane sulfonic acid. The object was to maintain the resin in a shrunken form during the filling process. This resin filled column was then coupled to the inlet of column A and the whole assembly pumped with water in a direction opposite to its normal use direction to displace MSA from the entrance section of the device and to cause the resin in the entrance section to swell and thereby favor a good contact between the entrance electrode and the resin.

The final step in preparing the device for use was the conversion of a portion of column B to the hydroxide form. In the case of the anion device, this step was accomplished chemically by pumping reagent (acid) to the device. In the case of the cation device, this was accomplished electrochemically by polarizing the device and pumping water through it. Current (2 mA) was passed through the device for one hour to inject hydroxide ion into the suppressor section. The device was now ready for testing.

EXAMPLE 8

Cation Analysis

The same arrangement of the device of FIG. 1 with the various other chromatographic elements of the system is used with the reversal of other polarities and type of ion exchange resin.

With the device so polarized, and water flowing at 1 ml/min., various test mixtures were injected and the chromatograms obtained.

The conditions of the various runs are summarized below and the chromatograms shown in FIGS. 9–11.

For FIG. 9, the conditions were (1) power-2 mA; 368 V, and (2) sample sodium fluoride and potassium nitrate 0.0005 M in each.

For FIG. 10, the conditions were (1) power-0.9 mA; 222 V, and (2) sample as in FIG. 9.

For FIG. 11, the conditions were (1) power-0.9 mA; 222 V, and (2) sample lithium chloride, sodium fluoride, potassium nitrate, 0.00033M in each.

EXAMPLE 9

In this example, a flow-through sponge-like ion exchange bed is formed, a portion of which is used as the substrate for anion exchange latex and the remainder as the suppressor component of an Ion Reflux device.

Styrene and divinyl benzene are copolymerized in the presence of an appropriate catalyst and a porogen. A porogen is an added material which, when removed after the polymerization is complete, creates a macroporosity in the polymerized structure. This porosity should be such that it provides for ready flow of liquids through the polymer phase while at the same time providing adequate areas of contact between the polymer and liquid phase. The porogen can be a finely divided solid which can be easily removed by dissolution in acid or base (e.g., calcium carbonate or silica) or it can be a solvent which is rejected by the polymer as it forms and is subsequently displaced by another solvent or water. Suitable liquid porogens include an alcohol such as dodecyl alcohol, e.g. used in the manner discribed in *Analytical Chemistry,* Vol. 68, No. 2, pp. 315–321, Jan. 15, 1996.

After the porogen is removed, the polymer is sulfonated by commonly known sulfonating agents such as concentrated sulfuric acid or chloro sulfonic acid.

A suitable shape for the polymer is a cylindrical rod which, after sulfonation and conversion to a suitable metal ion form can be placed in the bore of a chromatography column typically 4 mm in internal diameter. Preferably the ion exchange rod is introduced into the column in a slightly shrunken form so that in its typical use environment it swells to form a tight fit with the wall of the column. Excess rod is trimmed from the end of the column.

Anion exchange latex is then carefully introduced into one portion of the column to deposit latex on that portion but not on the remaining portion which acts as the suppressor section. The column is then equipped with porous platinum electrodes and end fittings. As a final step, a part of the untreated section closest to the device outlet is converted to the hydronium form, either by treating it with the appropriate amount of acid, or by electrochemically displacing potassium ions with hydronium ions.

EXAMPLE 10

In this example, a film-type ion exchange bed is formed, a portion of which is used as the substrate for an anion exchange latex and the remainder as the suppressor component of an ion reflux device.

A strip of cation exchange membrane in an appropriate metal ion form is rolled on to a solid spindle whose diameter is approximately 5 mm. The width of the film and the length of the spindle are preferably the same. Enough film is added to the spindle to give a final diameter of approximately 15 mm. The film/spindle assembly is then placed in a snug fit within a hollow cylinder of the same length as the spindle.

Anion exchange latex is then carefully introduced into one portion of the column/spindle assembly to deposit latex on that portion but not on the remaining portion which acts as the suppressor section. The spindle/column assembly is then equipped with porous platinum electrodes and end fittings. As a final step, a part of the untreated section closest to the device outlet is converted to the hydronium form, either by treating it with the appropriate amount of acid, or by electrochemically displacing potassium ions with hydronium ions.

What is claimed is:

1. A method of anion analysis using a flow-through bed of cation exchange material including exchangeable cations, said bed having a first and second section arranged in series, said method comprising (a) flowing an aqueous feed stream through said first bed section while applying an electrical potential to a cathode in electrical communication therewith to generate hydroxide ions in said aqueous stream and assist in displacing some of said exchangeable cations into said aqueous stream to form an aqueous eluent stream comprising a cation hydroxide base, (b) flowing a liquid sample stream containing anions to be detected and said eluent through a chromatographic separator portion of said first bed section, said last named section further comprising anion exchange material, to separate said anions to be detected, (c) flowing said aqueous separated anion stream through said second bed section substantially free of anion exchange material and including exchangeable hydronium ions, while applying an electrical potential to an anode in electrical communication with said second bed section and to generate hydronium ions in said separated anion aqueous stream near said anode, to convert said base to weakly ionized form, and displacing some of said exchangeable hydronium ions with cations from said base, said aqueous stream exiting said second section as a suppressed effluent, said first and second bed sections forming a cation path through said cation exchange material between said anode and cathode with said cations electromigrating from said second bed section to said first bed section along said cation path in the opposite direction to said aqueous feed stream to replenish exchangeable cations displaced from said first bed in step (a), and (d) flowing said suppressor effluent stream past a detector in which the separated anions in said suppressor effluent are detected.

2. The method of claim 1 in which said chromatographic separator portion extends to a region proximal said cathode.

3. The method of claim 1 in which said cation exchange material is substantially continuous between said cathode and anode.

4. The method of claim 1 further comprising flowing the aqueous feed stream through a hydronium ion cation exchange bed prior to step (a) to convert salts in sample stream to their acid form.

5. The method of claim 1 further comprising pressurizing said bed in the direction opposite to the flow of said aqueous feed stream.

6. The method of claim 1 in which said bed comprises a cation exchange resin packed bed.

7. The method of claim 1 in which the cation exchange material in said chromatographic separator portion comprises cation exchange resin particles in a packed bed and said anion exchange material comprises fine anion exchange resin particles coated onto said cation exchange resin particles.

8. The method of claim 1 in which said aqueous bed stream is electrolyzed during application of said electrical potential to generate hydrogen and oxygen gases, said method further comprising pressurizing said bed prior to detection in step (d) to minimize adverse effects of said gases on detection of said anions.

9. The method of claim 1 in which said detection in step (d) is by electrical conductivity detection.

10. A method of cation analysis using a flow-through bed of anion exchange material including exchangeable anions, said bed having a first and second section arranged in series, said method comprising (a) flowing an aqueous feed stream through said first bed section while applying an electrical potential to an anode in electrical communication therewith to generate hydronium ions in said aqueous stream and assist in displacing some of said exchangeable anions into said aqueous stream to form an aqueous eluent stream comprising an acid, (b) flowing a liquid sample stream containing cations to be detected and said eluent through a chromatographic separator portion of said first bed section, said last named section further comprising cation exchange material, to separate said cations to be detected, (c) flowing said aqueous separated cation stream through said second bed section substantially free of cation exchange material and including exchangeable hydroxide ions, while applying an electrical potential to a cathode in electrical communication with said second bed section and to generate hydroxide ions in said separated cation aqueous stream near said cathode, to convert said acid to weakly ionized form, and displacing some of said exchangeable hydroxide ions with anions from said acid, said aqueous stream exiting said second section as a suppressed effluent, said first and second bed sections forming an anion path through said anion exchange material between said cathode and anode with said anions electromigrating from said second bed section to said first bed section along said anion path in the opposite direction to said aqueous feed stream to replenish exchangeable anions displaced from said first bed in step (a), and (d) flowing said suppressor effluent stream past a detector in which the separated cations in said suppressor effluent are detected.

11. The method of claim 10 in which said chromatographic separator portion extends to a region proximal said anode.

12. The method of claim 10 in which said anion exchange material is substantially continuous between said anode and cathode.

13. The method of claim 10 further comprising flowing the aqueous feed stream through a hydroxide ion anion exchange bed prior to step (a) to convert salts in sample stream to their base form.

14. The method of claim 10 further comprising pressurizing said bed in the direction opposite to the flow of said aqueous feed stream.

15. The method of claim 10 in which said bed comprises an anion exchange resin packed bed.

16. The method of claim 10 in which the anion exchange material in said chromatographic separator portion comprises anion exchange resin particles in a packed bed and said cation exchange material comprises fine cation exchange resin particles coated onto said anion exchange resin particles.

17. The method of claim 10 in which said aqueous bed stream is electrolyzed during application of said electrical potential to generate hydrogen and oxygen gases, said method further comprising pressurizing said bed prior to detection in step (d) to minimize adverse effects of said gases on detection of said anions.

18. The method of claim 10 in which said detection in step (d) is by electrical conductivity detection.

19. An apparatus for anion analysis comprising (a) a sample injection port (b) a flow-through bed of cation exchange material including exchangeable cations, said bed having first and second bed sections arranged in series, said first bed section being in fluid communication with said sample injection port and further comprising a chromatographic separator portion including anion exchange material capable of separating anions in an aqueous sample stream flowing through said chromatographic separator portion, said second bed portion being substantially free of anion exchange material, (c) first and second electrodes in electrical communication with said first and second bed sections, respectively, the cation exchange material in said first and second bed sections forming a cation path through said cation exchange material between said first and second electrodes, and (d) a power supply for applying a potential between said first and second electrodes.

20. The apparatus of claim 19 further comprising (e) a detector in fluid communication with said second bed section.

21. The apparatus of claim 20 in which said detector is an electrical conductivity detector.

22. The apparatus of claim 20 further comprising (e) means for maintaining under pressure an aqueous stream flowing through said bed to said detector.

23. The apparatus of claim 19 in which said bed comprises a cation exchange resin packed bed.

24. The apparatus of claim 19 in which said chromatographic separator portion contacts said cathode.

25. The apparatus of claim 19 in which said cation exchange material is substantially continuous between said cathode and anode.

26. The apparatus of claim 19 in which the cation exchange material in said chromatographic separator portion comprises cation exchange resin particles in a packed bed and said anion exchange material comprises fine anion exchange resin particles coated onto said cation exchange resin particles.

27. The apparatus of claim 19 in which said first bed section includes a region substantially free of anion exchange material.

28. The apparatus of claim 19 further comprising a cation exchanger including exchangeable hydronium ions in fluid communication with and upstream of said flow-through bed.

29. The apparatus of claim 19 in which said cation exchange material is in direct contact with said cathode and anode.

30. An apparatus for cation analysis comprising (a) a sample injection port (b) a flow-through bed of anion exchange material including exchangeable anions, said bed having first and second bed sections arranged in series, said first bed section being in fluid communication with said sample injection port and further comprising a chromatographic separator portion including cation exchange material capable of separating cations in an aqueous sample stream flowing through said chromatographic separator portion, said second bed portion being substantially free of cation exchange material, (c) first and second electrodes in electrical communication with said first and second bed sections, respectively, the anion exchange material in said first and second bed sections forming an anion path through said anion exchange material between said first and second electrodes, and (d) a power supply for applying a potential between said first and second electrodes.

31. The apparatus of claim 30 further comprising (e) a detector in fluid communication with said second bed section.

32. The apparatus of claim 31 in which said detector is an electrical conductivity detector.

33. The apparatus of claim 31 further comprising (e) means for maintaining under pressure an aqueous stream flowing through said bed to said detector.

34. The apparatus of claim 30 in which said bed comprises an anion exchange resin packed bed.

35. The apparatus of claim 30 in which said chromatographic separator portion extends to a region proximal said anode.

36. The apparatus of claim 30 in which said anionic exchange material is substantially continuous between said anode and cathode.

37. The apparatus of claim 30 in which the anionic exchange material in said chromatographic separator portion comprises anion exchange resin particles in a packed bed and said cation exchange material comprises fine cation exchange resin particles coated onto said anion exchange resin particles.

38. The apparatus of claim 30 in which said first bed section includes a region substantially free of cation exchange material.

39. The apparatus of claim 30 further comprising an anion exchanger including exchangeable hydroxide ions in fluid communication with and upstream of said flow-through bed.

40. The apparatus of claim 30 in which said anion exchange material is in direct contact with said cathode and anode.

* * * * *

UNITED STATES PATENT AND TRADEMARK OFFICE
CERTIFICATE OF CORRECTION

PATENT NO : 5,914,025
DATED : June 22, 1999
INVENTOR(S) : SMALL

It is certified that error appears in the above-identified patent and that said Letters Patent is hereby corrected as shown below:

Column 3, line 54, delete "gases hydrogen" and insert therefor –gases (hydrogen–.

Column 10, line 40, delete "(NSA)" and insert therefor --(MSA)--.

IN THE CLAIMS:

Claim 23 should be claim 21.
Claim 21 should be claim 22.
Claim 22 should be claim 23.

Claim 34 should be claim 32.
Claim 32 should be claim 33.
Claim 33 should be claim 34.

Signed and Sealed this

Nineteenth Day of September, 2000

Attest:

Q. TODD DICKINSON

Attesting Officer      Director of Patents and Trademarks